United States Patent [19]

Rogic et al.

[11] 4,045,422

[45] Aug. 30, 1977

[54] SYNTHESIS OF α-NITROSOKETAL DIMERS

[75] Inventors: Milorad M. Rogic, Whippany;
Michael D. Swerdloff, Parsippany;
Timothy R. Demmin, Morris Plains,
all of N.J.

[73] Assignee: Allied Chemical Corporation, Morris
Township, N.J.

[21] Appl. No.: 600,666

[22] Filed: July 31, 1975

Related U.S. Application Data

[63] Continuation-in-part of Ser. No. 460,836, April 15, 1974, abandoned.

[51] Int. Cl.$^2$ .................. C07C 105/00; C07C 131/00
[52] U.S. Cl. .............................. 260/143; 252/429 A;
260/239.3 R; 260/340.3; 260/340.5 R;
260/340.6; 260/340.7; 260/464; 260/465.4;
260/534 R; 260/566 A; 260/586 R; 260/615 A;
260/340.9 R
[58] Field of Search ........................................ 260/143

[56] References Cited

U.S. PATENT DOCUMENTS

| 2,371,418 | 3/1945 | Beckham et al. | 260/647 |
| 2,394,430 | 2/1946 | Crowder et al. | 260/566 A |
| 3,222,380 | 12/1965 | Manning et al. | 260/143 X |
| 3,647,777 | 3/1972 | Hudson et al. | 260/143 |

Primary Examiner—Floyd D. Higel
Attorney, Agent, or Firm—Arthur J. Plantamura; Roger H. Criss

[57] ABSTRACT

Ketals of α-oximinoketones and methods for the preparation of these compounds including intermediates are described. The compounds disclosed include both α-oximinoketals and cyclic ketals of α-oximinoketones. Also disclosed is a class of α-nitrosoketal dimers produced during the synthesis of the corresponding α-oximinoketals and the method for their preparation.

5 Claims, No Drawings

SYNTHESIS OF α-NITROSOKETAL DIMERS

This is a continuation-in-part of application Ser. No. 460,836, filed Apr. 15, 1974, now abandoned.

FIELD OF THE INVENTION

This invention describes novel ketals of various α-oximinoketones, methods for the preparation of these compounds and includes novel intermediates formed during the production thereof. The novel class of compounds disclosed herein includes both the α-oximinoketals, as well as the cyclic ketals of α-oximinoketones. This invention also discloses a novel class of α-nitrosoketal dimers, which can be regarded as the intermediates in the production of the corresponding α-oximinoketals, and particularly it discloses novel methods for the production of the said α-nitrosoketal dimers.

Beckman fragmentation of these novel ketals of α-oximinoketones, particularly those of α-oximinocyclohexanone, α-oximinocyclopentenone, α-oximinocyclooctanone, α-oximinocyclodecanone, etc. provides the corresponding alkyl ω-cyanoalkanoates which are convenient intermediates for the production of either cyclic lactams or polyamides and amino acids. Similarly, direct nitrosolysis of the corresponding α-nitrosoketal dimers provides the same alkyl ω-cyanoalkanoates as above.

SUMMARY OF THE INVENTION

The novel α-nitrosoketal dimers, which can be used as intermediates for the synthesis of the α-oximinoketals, may be characterized by the formula:

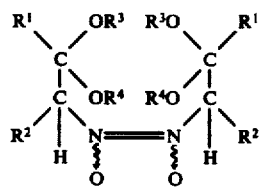

which for convenience of notation will henceforth be written as:

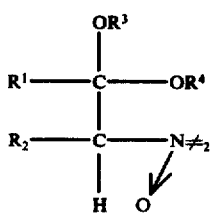

with an implicit understanding that the corresponding dimer may be either a dl-pair, or meso compound of either Z- or E-dimers where Z- and E- refer to the cis- or trans- configuration of the two oxygen atoms attached to the N=N grouping, wherein: $R^1$ and $R^2$ are selected from the group consisting of $C_1$–$C_{10}$ alkyl or phenyl and/or combinations thereof, or in combination, together represent a part of the $C_5$, $C_6$, $C_7$, $C_8$, $C_9$, $C_{10}$, $C_{11}$, and $C_{12}$ cyclic ring structure, and $R^3$ and $R^4$ are independently selected from the group consisting of $C_1$–$C_{10}$ alkyl, cyclohexyl and $C_1$–$C_4$ alkyl substituted cyclohexyl radicals.

The novel ketals of α-oximinoketones described in the present invention may be characterized by the following formula:

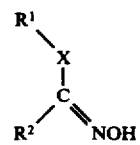

wherein: $R^1$ and $R^2$ are selected from the group consisting of $C_1$–$C_{10}$ alkyl or phenyl and/or combinations thereof, or in combination together represent a part of the $C_5$–$C_{12}$ cyclic ring structure; and X is a member of the group consisting of:

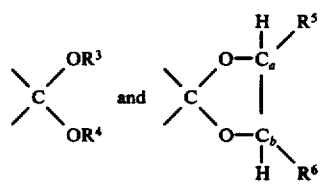

wherein $R^3$ and $R^4$ are independently selected from the group consisting of $C_1$–$C_{10}$ alkyl, cyclohexyl and $C_1$–$C_4$ alkyl substituted cyclohexyl radicals, and $R^5$ and $R^6$ are (when $R^1$ and $R^2$ in the parent formula above are part of the $C_6$-cyclic ring structure) independently hydrogen, phenyl, $C_1$–$C_{10}$ alkyl, or in combination with $C_a$ and $C_b$ form a cyclohexyl radical.

Illustrative nitrosoketal dimers include:

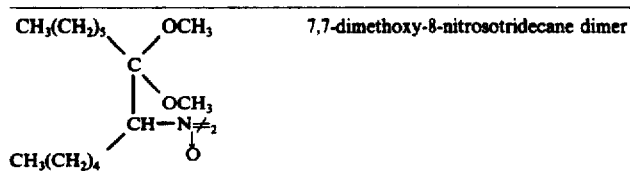

7,7-dimethoxy-8-nitrosotridecane dimer

-continued

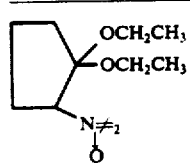 1,1-dimethoxy-2-nitrosocyclopentane dimer

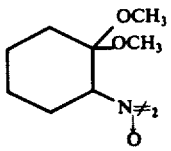 1,1-dimethoxy-2-nitrosocyclohexane dimer

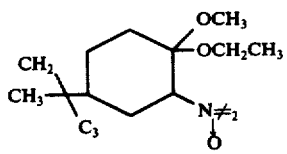 1-methoxy-1-ethoxy-2-nitroso-4-t-butyl-cyclohexane dimer

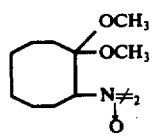 1,1-dimethoxy-2-nitrosocyclooctane dimer

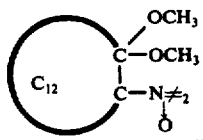 1,1-dimethoxy-2-nitrosocyclododecane dimer

Illustrative α-oximinoketal compositions include:

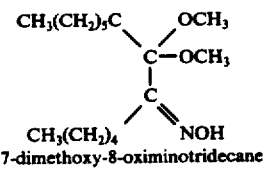
7,7-dimethoxy-8-oximinotridecane

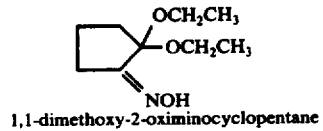
1,1-dimethoxy-2-oximinocyclopentane

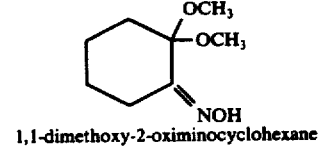
1,1-dimethoxy-2-oximinocyclohexane

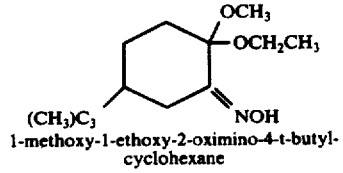
1-methoxy-1-ethoxy-2-oximino-4-t-butyl-cyclohexane

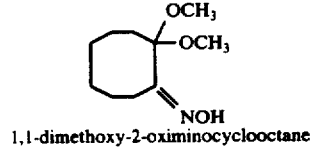
1,1-dimethoxy-2-oximinocyclooctane

-continued

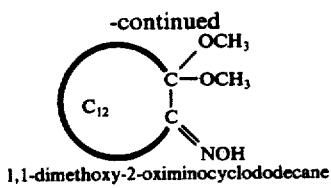
1,1-dimethoxy-2-oximinocyclododecane

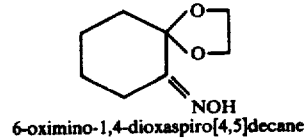
6-oximino-1,4-dioxaspiro[4,5]decane

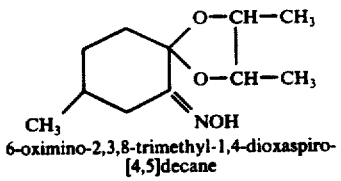
6-oximino-2,3,8-trimethyl-1,4-dioxaspiro-[4,5]decane

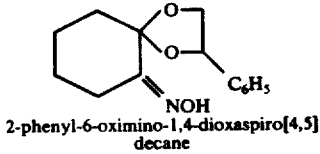
2-phenyl-6-oximino-1,4-dioxaspiro[4,5]decane

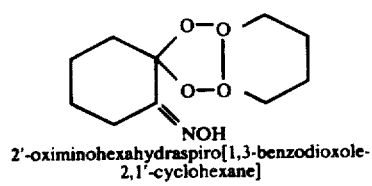
2'-oximinohexahydraspiro[1,3-benzodioxole-2,1'-cyclohexane]

-continued

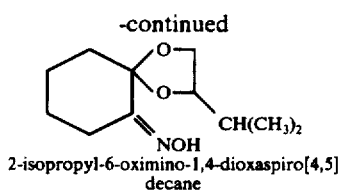
2-isopropyl-6-oximino-1,4-dioxaspiro[4,5]decane

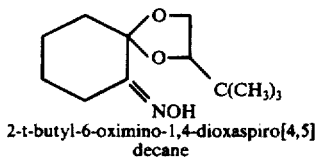
2-t-butyl-6-oximino-1,4-dioxaspiro[4,5]decane

The novel dimer compositions of the present invention may be prepared by nitrosating alkoxyalkenes of the formula:

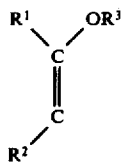

wherein:

$R^1$ and $R^2$ are selected from the group consisting of $C_1$–$C_{10}$ alkyl or phenyl and/or combinations thereof, or in combination together represent a part of the $C_5$–$C_{12}$ cyclic ring structure, and $R^3$ is selected from the group consisting of $C_1$–$C_{10}$ alkyl, cyclohexyl, and $C_1$–$C_4$ substituted cyclohexyl radicals; with at least one molar equivalent of an alkyl nitrite of the formula $$R^4ONO$$

either in the absence of other solvents, or in an inert solvent in either case in the presence of catalytic amounts of a suitable acid catalyst, wherein $R^4$ is selected from the group consisting of $C_1$–$C_{10}$ alkyl, cyclohexyl and $C_1$–$C_4$ alkyl substituted cyclohexyl radicals, and isolating the dimer product(s) thus formed.

These dimers may be readily converted to the corresponding α-oximinoketals by isomerizing the dimers and isolating desired products.

However, in accordance with the method of the present invention, it is not necessary to isolate and purify the dimer product in order to produce the desired oximino ketal product. Thus, satisfactory yields of the α-oximinoketals may be obtained by nitrosating the previously described alkoxyalkenes either with an excess of an alkyl nitrite in the absence of other solvent, or in an inert solvent, removing the excess of alkyl nitrite, adding an inert solvent, isomerizing the remaining residue, and isolating the desired product.

In addition to producing these novel α-oximinoketals by nitrosating with alkyl nitrites and isomerizing, it is possible to perform the desired nitrosation using at least one molar equivalent each of a nitrosyl halide, a base and an alcohol of the formula $R^4OH$ where $R^4$ is as previously defined; and isolating the desired product.

The novel cyclic ketals of α-oximinocyclohexanone disclosed herein are similarly prepared by nitrosating, in an inert solvent a cyclohexanone compound of the formula

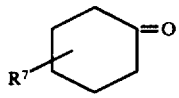

wherein $R^7$ is a $C_1$–$C_4$ alkyl radical, with at least one molar equivalent of each of a nitrosyl halide, an acid, and a vicinal diol of the formula

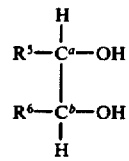

where $R^5$ and $R^6$ are as previously defined; neutralizing the acidic intermediate thus produced; and isolating the resulting cyclic ketal of α-oximinocyclohexanone.

DESCRIPTION OF THE PREFERRED EMBODIMENTS

In accordance with the method of the present invention, the novel α-nitrosoketal dimers are produced by the nitrosation of the corresponding alkoxyalkenes. The novel α-oximinoketals are produced either by isomerization of the corresponding nitroso dimers, or directly from the alkoxyalkenes by nitrosation and isomerization without isolation of the intermediates involved. Additionally, the novel cyclic ketals of α-oximinocyclohexanone can be produced directly from cyclohexanone by nitrosation in the presence of a suitable vicinal diol.

The alkoxyalkenes used as starting materials in this invention may be prepared using a variety of methods such as by the acid catalyzed elimination of the alcohol from the corresponding ketals, as represented by the equation:

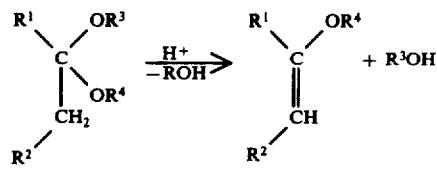

wherein $R^1$, $R^2$, $R^3$ and $R^4$ are as previously defined. Thus $R^1$ and $R^2$ may be any $C_1$–$C_{10}$ alkyl radical, phenyl group, or in combination together may be a part of $C_5$–$C_{12}$ cyclic structure.

The nitrosation of alkoxyalkenes may be carried out using at least one molar equivalent, preferably 3–10 molar equivalent of a suitable nitrosating reagent in the absence of other solvent and in the presence of a catalytic amount, preferably between 0.01–0.1 molar equivalent, of a suitable acid. Suitable nitrosating agents include alkyl nitrites of the formula $R^4ONO$, where $R^4$ is as previously defined. The suitable acid catalysts are sulfur trioxide, sulfuric acid, oleum, boron trifluoride etherate, alkyldialkoxycarbonium fluoroborates, preferably boron trifluoride etherate or alkyldimethoxycarbonium fluoroborates.

Thus, preparation of the corresponding α-nitrosoketal dimers may be represented with the equation:

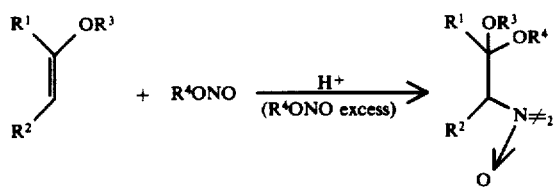

wherein $R^1$, $R^2$, $R^3$ and $R^4$ are as previously defined. The nitrosation reaction may be carried out between $-70°$ - $+25°$, preferably at $-30°$ - $0°$, and would depend on particular system employed. The isolation of the nitroso dimer may be accomplished either by filtration or by evaporation of the excess of the alkyl nitrite used.

Alternatively, the nitrosation reaction with alkyl nitrites may be carried out in any suitable inert solvent using only one, preferably 1.10–1.20 molar equivalents of an alkyl nitrite and the suitable acid catalyst. Suitable solvents include ether, chloroform, organic sulfones, organic nitro compounds, etc., however, liquid sulfur dioxide is preferred. The amount of solvent employed should be sufficient to bring the desired course of the reaction. When solvents other than sulfur dioxide are employed, the presence of acid catalyst, e.g., sulfur trioxide, sulfuric acid, boron trifluoride etherate, is required; when sulfur dioxide is employed, such a catalyst is preferred but not essential to the course of the reaction.

The nitrosation with alkyl nitrites in the presence of a solvent may be carried out using a wide range of temperatures, depending on the solvent used and the nature of the alkyl nitrite. Using $SO_2$ as solvent, the preferred temperature range is between '30° and +25° C., although the temperature between the freezing and boiling points of the solvent could be used. Similarly, nitrosation with alkyl nitrites in the absence or in the presence of other solvent, may be carried out either at atmospheric pressure or higher, preferably between atmospheric pressure and 200 psi.

If recovery of the thus formed nitroso dimer is desired, it may be readily isolated by evaporation of the solvent (including the excess alkyl nitrite), in the presence of small amount of sodium bicarbonate or other base which is added to assure the neutralization of any acid catalyst used. The desired material is then recovered by filtering from a solvent in which the particular nitroso dimer has little or no solubility.

The isomerization of thus produced nitroso dimers to the corresponding α-oximinoketals may be carried out with or without the previously described isolation of the dimer. This isomerization may be accomplished using a variety of methods, and can be schematically represented by the following equations:

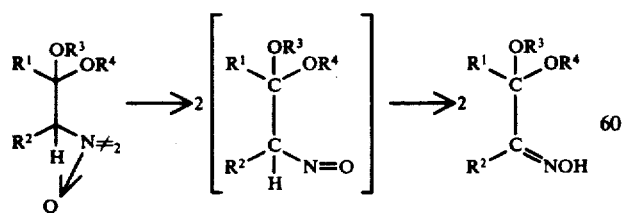

wherein $R^1$, $R^2$, $R^3$ and $R^4$ are as previously described.

In accordance with the present invention, the dimer may be heated above its melting point until such time as the color of the melt changes from blue, indicative of the presence of the corresponding monomeric nitroso compound, to either colorless or slightly yellow. Subsequent cooling provides the desired α-oximinoketals which can be further purified by conventional technique.

Alternatively, the nitroso dimers may be isomerized by heating in solvents, such as pentane, benzene, heptane, toluene, methanol, ethanol, chloroform, etc., at a temperature below the melting point of the compound. A further isomerization procedure comprises a catalytic reaction using either inert or hydroxylic solvents as above in the presence of a catalytic amount of base. In this case the isomerization can be accomplished either at room temperature or by heating.

If the preparation of the nitroso dimer is carried out in a solvent and the dimer is not isolated, the isomerization can be achieved by heating the reaction mixture after completion of the nitrosation reaction, either in the presence of the acid catalyst used in the nitrosation reaction, or under slightly basic conditions after neutralization of the acid catalyst with various bases, such as metal alkoxides. Alternatively, in accordance with the preferred method, the sulfur dioxide or excess alkyl nitrite, is displaced by a solvent such as methanol, ethanol, pentane, benzene, heptane, toluene, or chloroform, and the isomerization is then achieved by heating, or as described above, in the presence of catalytic amount of base. In either case, the desired α-oximinoketal is isolated after removal of solvent, as for example, by crystallization.

In the case of nitrosation of alkoxyalkenes with a nitrosyl halide, preferably nitrosyl chloride, a corresponding halo substituted compound is formed as an intermediate which is then treated, without isolation, in the presence of at least one molar equivalent of each of base and an alcohol of the formula $R^4OH$ where $R^4$ is as previously defined. Preferably 2–3 molar equivalents of the alcohol are employed. Alternatively, the nitrosation reaction may be carried out in the presence of the alcohol, in which case the base is added after complete addition of the nitrosyl halide and worked-up as before.

Schematically, this reaction may be represented by the following equations using nitrosyl chloride as the nitrosating reagent.

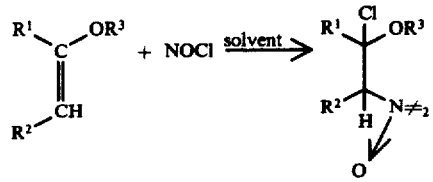

wherein $R^1$, $R^2$, $R^3$ and $R^4$ are as previously defined. This reaction may be carried out in any of the previously disclosed inert solvents; however, the preferred solvent for this particular reaction is ether. Suitable bases include sodium methoxide, pyridine, triethylamine, and preferably a solution of sodium hydroxide in the R⁴OH alcohol. The reaction temperature is not critical and preferably, when ether is used as solvent, will be between −20° and 30° C. Pressures within the range of one atmosphere to 200 psi may be employed. The reaction time is not critical and is selected to ensure complete reaction. After separation of the halide salt the reaction product, the corresponding α-oximinoketal, may be isolated by evaporation of the solvent and crystallization.

The synthesis of the novel cyclic ketal derivatives of α-oximinocyclohexanone is achieved by the nitrosation in the presence of an inert solvent of a cyclohexanone compound of the formula

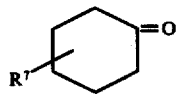

wherein $R^7$ is as previously defined, with at least one molar equivalent of each of a nitrosyl halide, an acid, and a vicinal diol of the formula

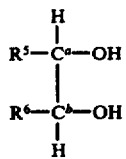

where $R^5$ and $R^6$ are as previously defined, neutralizing the acid salts thus formed; and isolating the desired product. Schematically, the reaction proceeds as follows:

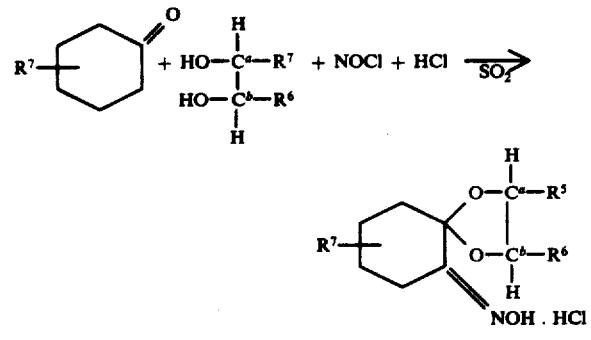

wherein $R^5$, $R^6$, $R^7$ and $C^a$ and $C^b$ are as previously defined. The nitrosation reaction may be carried out either with a nitrosyl halide, preferably nitrosyl chloride, or with an alkyl nitrite in the presence of hydrogen halide to produce the nitrosyl halide in situ. In either case, at least one molar equivalent nitrosating agent, preferably 1.10–1.50 molar equivalents nitrosating agent, is employed together with at least one additional mole, preferably one to two additional moles strong acid, preferably HCl. This reaction may be carried out in an inert solvent, preferably liquid sulfur dioxide. The reaction temperature may vary between about −70° and +50° C. with preferred range of −20° to +25° C. at pressures of one atmosphere to 200 psi.

The nitrosation is accomplished either by introducing the nitrosyl halide into a solution of the cyclohexanone in the solvent in the presence of an acid catalyst and the vicinal diol, or by addition of an alkyl nitrite to the same solution containing an additional equivalent of acid. In the latter case, the alkyl nitrite may be either derived from the corresponding vicinal diol or may be selected in such a way as to assure that the generated alcohol would not adversely compete with the glycol in the ketal formation. A suitable alkyl nitrite, for example, would be t-butyl nitrite.

The reaction is usually complete after addition of all the nitrosating agent; however, the reaction period may be extended with no deleterious results. The product may be isolated by removal of the solvent and any excess acid in vacuo at temperatures between about −70° and +10° C., preferably between −10° and +5° C., followed by neutralization of the acid salt in a solution of a solvent such as chloroform containing a suitable base such as anhydrous ammonia, ammonium hydroxide, pyridine, triethylamine, a solution of sodium methoxide, sodium hydroxide or moist sodium bicarbonate. The cyclic ketal thus produced is then isolated by filtering to remove the salts of neutralization and the solvent is then evaporated. The crude cyclic ketal derivative of α-oximinocyclohexanone may then be purified either by crystallization or by column chromatography. The synthesis of the novel cyclic ketal derivatives of α-oximinocyclohexanone has also been achieved by the nitrosation in the presence of an inert solvent of a cyclohexanone ketal of the formula:

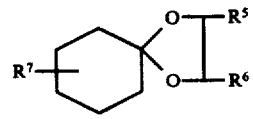

wherein $R^5$, $R^6$ and $R^7$ are as previously defined, with at least one molar equivalent of a nitrosyl halide and preferably one molar equivalent of an acid, neutralizing the acid salts thus formed; and isolating the desired product. Schematically, the reaction proceeds as follows:

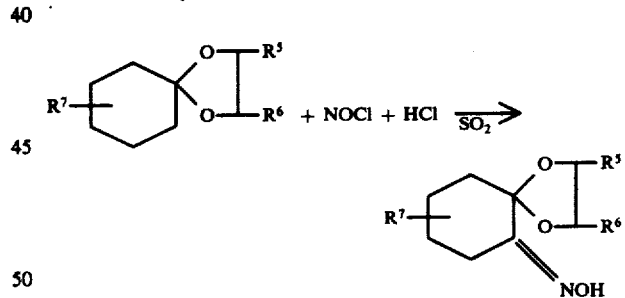

wherein $R^5$, $R^6$ and $R^7$ are as previously defined.

The invention will be further illustrated by the following Examples.

EXAMPLE 1

Production of 1,1-dimethoxy-2-nitrosocyclohexane dimer using excess of methyl nitrite as solvent Methyl nitrite (125 g, 2.05 mole) was distilled into a 500 ml flask equipped with a mechanical stirrer, addition funnel, dry ice condenser, $N_2$ atmosphere and a bath maintained at −20° C. 20% Oleum (0.325 ml, 1 mole % based on amount of 1-methoxycyclohexene used) was added. 1-Methoxycyclohexene (75.4 g, 0.674 mole) was added dropwise over 2.5 hours with stirring. The reaction mixture was a heavy suspension of a white solid in a blue-green liquid. The catalyst was neutralized by sodium bicarbonate (6.5 g) with the addition of petroleum ether (b.p. 30° - 60° C.) to facilitate stirring. Excess methyl nitrite was allowed to distill off, and the reaction mixture filtered and the white solid washed with petroleum ether. Evaporation of the filtrate in vacuum is carried out to recover partially dissolved product. The combined crude solid dimer, 113.8 g, was according to nmr analysis essentially pure 1,1-dimethoxy-2-nitrosocyclohexene dimer. The inorganic materials can be removed by dissolving the crude dimer in freshly distilled methylene chloride, filtering and removing the solvent at 0° C. Such a dimer is white powder m.p. 108°-110°.

EXAMPLE 2

Production of 1,1-dimethoxy-2-nitrosocyclohexane dimer

Methyl nitrite (29.75 g., 0.487 mole) was distilled into 250 ml. of sulfur dioxide maintained at −78° C. in a 1000 ml. three-neck flask equipped with a mechanical stirrer, an addition funnel-dry nitrogen inlet and a dry-ice/acetone condenser. Freshly distilled boron trifluoride-etherate (0.25 ml., 0.28 g., 2.0 × 10⁻³ mole) was quickly added via syringe and the light yellow solution was warmed to −15° C. with a bath of dry ice/carbon tetrachloride. The nitrogen inlet was then placed in the condenser and 1-methoxycyclohexene (45.8 g., 0.407 mole) was added dropwise over 20 minutes to the stirred reaction mixture. After the addition was complete, stirring was continued for an additional 20 minutes at −15° C. and the deep blue-green solution rapidly turned a light yellow-green. The cooled (−78° C.) reaction mixture was quickly poured into 200 ml. of cold pentane containing sodium bicarbonate (1-2 g.) and then thoroughly evaporated at 20° C. The yellow-green gummy residue was triturated with several portions of pentane (150 ml. each) at 0° C., re-evaporated each time, and finally allowed to warm to room temperature under 300 ml of pentane with occasional swirling over 45 minutes. The off-white solid was filtered, rinsed with cold pentane, stirred with 150 ml. of water at 0° C. and then filtered and dried in vacuo to give 35.4 g. (50.1%) of the nitroso dimer, m.p. 108°-120° C.

EXAMPLE 3 a. Preparation of Ethyldimethoxycarbonium Fluoroborate Catalyst*

In a dry reactor with an argon atmosphere, trimethylorthopropionate (b.p. 122° -125°C., 11.3 g., 84.3 moles) is cooled to −30° C. A mixture of BF₃·Et₂O (12.3 ml., 94.4 mmoles) and dry dichloromethane (10 ml.) is added over a 15 minute period with stirring. The reactor is warmed to ice-water bath temperature for 15 minutes. Dry ethyl ether (15 ml) is added and the reaction mixture is cooled to −70° C. The solvents are decanted from the solid, brown product which is then washed at −70° C. with a mixture of dichloromethane (10 ml.) and ethylether (10 ml.). After decantation, the product is dried at RT/<1mm Hg to an off-white solid. It is dissolved in dichloromethane (30 ml) to a yellow-brown solution and stored at RT under a slight pressure of argon. Its concentration was determined to be two mmole/ml by the use of nmr and an internal standard (chloroform). When used as a catalyst an aliquot is removed by syringe. The structure

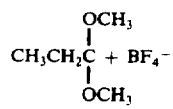

was confirmed by nmr.

*In preparing this catalyst the procedure disclosed in R. F. Borch, JOC, Vol. 34, No. 3, p. 627, March (1969), R. F. Borch, JACS/90;19/Sept. 11 (1968), p. 5303 was utilized.

b. 1,1-dimethoxy-2-nitrosocyclohexane dimer was prepared by the procedure described in Example 1 with the exception that one mole percent diethoxycarbonium fluoroborate was used as a catalyst. The essentially pure dimer was recovered as product and its structure was confirmed by IR and nmr.

EXAMPLE 4

1-Ethoxy-1-methoxy-2-nitrosocyclohexane dimer was prepared according to the procedure described in Example 1 from the reaction of 1-ethoxycyclohexene (20.4 g., 0.162 moles) and excess methylnitrite (2.5 g., 0.414 mole). In this instance, only about 25% of the dimer (5.9 g.) was recovered as precipitate with the major portion (18.9 g.) being recovered by flash evaporation of the wash liquors at 25° C. The recovered products were essentially the same and IR and nmr confirmed the structure as being essentially pure dimer.

EXAMPLE 5

1,1-Dimethoxy-2-nitrosocyclopentane dimer was prepared as in Example 1 by reacting 1-methoxycyclopentene (15.9 g., 0.162 mole) with an excess of methylnitrite (29.7 g., 0.48 mole) using 0.5 mole percent of 20% oleum as catalyst. The product (20.5 g.) was mostly the desired dimer with a small amount of 1,1-dimethoxy-2-oximinocyclopentane. An additional 5 grams of product were recovered by flash evaporation of the wash liquors. The structure was confirmed by IR and nmr.

When the product was allowed to stand for four days at room temperature in chloroform, it rearranged to 1,1-dimethoxy-2-oximinocyclopentane mp 79°-80° containing some methyl ester of 3-cyanobutyric acid.

EXAMPLE 6

Using the procedure described in Example 1, 1,1-dimethoxy-2-nitrosocylooctane dimer was prepared by reacting 1-methoxycyclooctene (18.5 g., 0.132 mole) with an excess of methylnitrite (25 g., 0.406 mole) in the presence of one mole percent of 20% oleum (0.065 ml) as catalyst. The precipitated dimer (17.5 grams) was recovered in the usual manner and its structure was confirmed by IR and nmr. An additional amount (10.6 g.) of dimer was recovered by flash evaporation of the wash liquors at ice-water temperature.

EXAMPLE 7

Using the procedure described in Example 1, 1,1-dimethoxy-2-nitrosocyclododecane dimer was prepared by reacting 1-methoxycyclododecene (25.8 g., 0.132 mole) with an excess of methylnitrite (25 g., 0.406 mole) in the presence of one mole percent of 20% oleum (0.065 ml) as catalyst. The structure of the dimer recovered (27.4g.) was confirmed by IR. This dimer was not soluble in chloroform, methanol, dichloromethane, 1,2-dichloroethane, isopropanol, DMSO, cyclohexane, nitromethane or benzene at room temperature. An additional 7 g. of product was recovered from the wash liquors.

EXAMPLE 8

Using the procedure described in Example 1, 2-methoxycamphene (18.9 g., 0.114 mole) was reacted with an excess of methylnitrite (25 g., 0.406 mole) in the presence of one mole percent of 20% oleum as catalyst. There was no indication of blue coloration (nitroso compounds) or a precipitate during the course of the reaction. After neutralization with sodium bicarbonate, the solvents were removed by flash evaporation yielding a pale yellow liquid (13.4 g). The yield is low due to analyses during the course of the run and also the possibility of volatilization during the evaporation of the solvents. IR and nmr indicate a mixture of products. The following components were identified by Finigan Mass Spec:

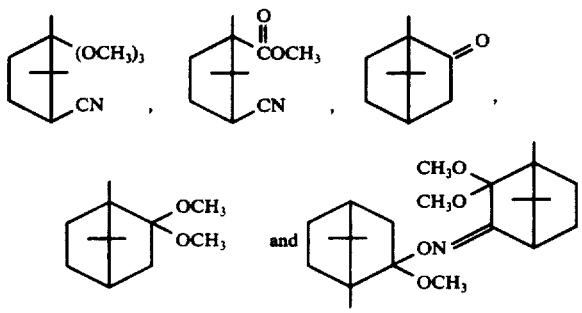

There was no evidence for 2,2-dimethoxy-3-oximinocamphor or 2,2-dimethoxy-3-nitrosocamphor or its dimer.

EXAMPLE 9

Using the procedure described in Example 1, 2,2-bis-(4-methoxycyclohex-2-enyl)propane (5 g., 0.0378 mole) was reacted with an excess of methylnitrite (25 g., 0.406 mole) in the presence of one mole percent of ethyldimethoxycarbonium fluoroborate as catalyst. While the reaction mixture was blue-green in color, there was no precipitate formed. The reaction mixture was neutralized with sodium bicarbonate and the excess methylnitrite was distilled from the reactor and stored for later reactions. The solid product was dissolved in 50 ml dichloromethane and filtered to remove inorganics. The product (7.1 g. pale green solid) was recovered by flash evaporation of the solvent. The nmr spectrum is compatible with the nitroso dimer structure but the IR also indicates the presence of nitroso groups. This is probably indicative of difficulties encountered in working with systems that can polymerize since possibly all of the nitroso groups cannot dimerize due to steric factors.

EXAMPLE 10

Using the procedure described in Example 1, attempted preparation of the 7,7-dimethoxy-6-nitrosotridecane dimer was carried out by reacting 7-methoxytridec-7-ene (28 g., 0.132 mole) with an excess of methylnitrite (25 g., 0.406 mole) in the presence of one mole percent of ethyldimethoxycarbonium fluoroborate as catalyst. After neutralization of the catalyst with sodium bicaronate, the excess methylnitrite was recovered by distillation. The reaction residue was dissolved in pentane (25 ml) and filtered to remove the inorganic material. On flashing off the pentane, a product (24.2 g.) was recovered which was not the dimer but mostly 7,7-dimethoxy-6-oximinotridecane. This structure was confirmed by nmr and IR. IR also indicates the presence of some carbonyl containing product which could be the methylester of octanoic acid. The yield of product is lower due to the removal of reaction mixture for analysis during the course of the reaction.

EXAMPLE 11

Using the procedure described in Example 10, a mixture (18.75 g., 0.135 mole) of 2-methoxyoct-2-ene (80%) and 2-methoxyoctene (20%) was reacted with an excess of methylnitrite (25 g., 0.406 mole) in the presence of one mole percent of ethyldimethoxycarbonium fluoroborate as catalyst. The product (23.3 g.) was a yellow liquid which, by nmr analysis, did not contain any dimer but was mostly a mixture of 3,3-dimethoxy-2-oximinooctane and 2,2-dimethoxy-1-oximinooctane. IR indicates the presence of an ester function which could mean that further reaction of the oximes may have taken place.

EXAMPLE 12

1,1-Dimethoxy-2-nitrosocyclohexane dimer (59.3 g.) as prepared in Examples 1 or 2 was dissolved in dichloromethane (200 ml) and allowed to stand at room temperature for three days. The tan solution was treated with decolorizing charcoal and filtered through a celite cake in an attempt to remove colored impurities. This was not successful. After flashing off the dichloromethane, the tan product (49.1 g.), m.p. 115°-116°, was essentially pure 1,1-dimethoxy-2-oximinocyclohexane by nmr and IR analysis.

EXAMPLE 13

Production of 1,1-dimethoxy-2-oximinocyclochexane 1,1-Dimethoxy-2-nitrosocyclohexane dimer (25.0 g., 72.2 mmole) prepared in Example 1 was suspended in 175 ml. of methanol and then made basic to pH 8 with sodium methoxide. The reaction mixture was stirred at 50° C. under a dry nitrogen atmosphere for 1¼ hours. After reducing the volume to 75-100 ml. on a rotary evaporator and slowly cooling to −20° C., the oxime was filtered off directly as clear colorless needles, 15.6 g., m.p. 116°-117°. An additional crop of slightly impure crystals, 4.2 g., m.p. 108°-115°, was collected by recrystallizing the residue from ether/pentane at −70° C. Total yield of oxime was 19.8 g. (79.2%).

EXAMPLE 14

1,1-Dimethoxy-2-nitrosocyclododecane dimer as prepared in Example 7, (31 g.) was heated (95° C.) in dry toluene (300 ml) for 1.5 hours with 150 mg. NaOCH₃ as catalyst. The suspended solid slowly dissolved in the blue-green reaction mixture which finally became yellow indicating that all of the nitroso groups had reacted. The cool reaction mixture was filtered through celite to remove inorganic material and the toluene was removed by flash evaporation. The cream colored solid (29.9 g.) was confirmed as 1,1-dimethoxy-2-oximinocyclododecane by nmr.

With more soluble nitroso dimers, such as 1,1-dimethoxy-2-nitrosocyclohexane, anhydrous methanol can be used as solvent in the above reaction. 1,1-Dimethoxy-2-nitrosocyclododecane was refluxed in methanol with catalytic quantities of sodium methoxide and was recovered unchanged. When n-butanol (b.p. 118°

C.) was used as solvent, the conversion to the oxime took place within 0.5 hours. However, there was interchange of butoxy groups for methoxy groups in the oxime so the use of n-butanol as solvent was discontinued.

EXAMPLE 15

2,2-Bis(4-methoxy-3-nitrosocyclohexyl)propane dimer (1 g.) as prepared in Example 9, was heated in dry toluene (10 ml) in the presence of catalytic amount of sodium methoxide. The blue-green solution turned yellow and a precipitate formed. The reaction mixture was refluxed for three hours. The light tan precipitate (0.57 g.) was recovered by filtration and IR indicates it is mainly 2,2-bis(4-methoxy-3-oximinocyclohexyl)propane. The filtrate was flash evaporated and the residue (0.2 g.) was similar to the starting nitroso dimer by nmr and IR analysis.

EXAMPLE 16

1,1-Dimethoxy-2-nitrosocyclooctane dimer (18.3 g.), prepared according to Example 6, was dissolved in dry toluene (150 ml.) at 45° C. and catalyzed with about 150 mg. of sodium methoxide. Within five minutes, the deep blue color changed to yellow and a reaction exotherm caused the temperature to rise to 56° C. The reaction mixture was stirred at ambient temperatures for 2.5 hours and the toluene flashed off after filtering off the inorganic materials using a celite cake. The pale yellow solid (15.3 g.) was identified as 1,1-dimethoxy-2-oximinocyclooctane by IR and nrm analysis. Some product was lost during the filtration.

EXAMPLE 17

1,1-Dimethoxy-2-oximinocyclohexane was produced directly from 1-methoxycyclohexene and methyl nitrite using the following procedure:

1,1-Dimethoxy-2-nitrosocyclohexane dimer was prepared as described in Example 1 from 1-methoxycyclohexene (46.8 g., 0.417 mole), methyl nitrite (30.6 g., 0.501 mole) and boron trifluoride-etherate (0.25 ml., 0.28 g., 2.0 × 10$^{-3}$ mole) in 250 ml. of sulfur dioxide. The crude nitroso dimer, 76.0 g. of a gummy yellow-green solid still containing traces of sulfur dioxide, was obtained by the method described earlier. Without purification, the dimer was subjected to isomerizing conditions in methanol/sodium methoxide solution. Filtration through celite (to remove colloidal solids that had formed) and evaporation afforded 66.0 g. of an off-white slightly moist solid. Recrystallization from 180 ml. of ether at −70° C. gave 26.8 g. (37.2%) of 1,1-dimethoxy-2-oximinocyclohexane as colorless fine needles, m.p. 112°-116° C. An additional 2.9 g. (4.0%) of slightly impure oxime was obtained from the mother liquor as a white powder, m.p. 105°-112° C.

EXAMPLE 18

1,1-Diethoxy-2-oximinocyclohexane was produced directly from 1-ethoxycyclohexene and nitrosyl chloride using the following procedure.

1-Ethoxycyclohexene (6.3 g., 50 mmole) was added to 100 ml. SO$_2$ maintained at about −50° C. Then 4.4 ml. (75 mmole) ethanol were added after which 3.2 ml. (70 mmole) nitrosyl chloride was added as a gas. When addition of the nitrosyl chloride was completed, the reaction mixture was concentrated, chloroform was added and the solution neutralized, with sodium bicarbonate in the presence of a small amount of water. The product was filtered and the crystals analyzed by nmr to indicate the presence of a major proportion of the desired product.

EXAMPLE 19

The procedure of Example 18 was repeated using ethyl ether as a solvent in place of SO$_2$. When the reaction was complete, the mixture was treated with additional ether, solid sodium bicarbonate and a small amount of water. The crystals collected after filtration and evaporation were examined by nmr and found to consist essentially of 1,1-diethoxy-2-oximinocyclohexane.

EXAMPLES 20–22

Methods similar to those employed in Examples 2 and 17–19 can be used to produce the following novel compounds.

| Ex. | Ether | Nitrosating Agent | Product |
|---|---|---|---|
| 20 | 1-methoxy-4-t-butylcyclohexene | ethyl nitrite | 1-methoxy-1-ethoxy-2-oximino-4-t-butylcyclohexane |
| 21 | 1-methoxy-5-phenylcyclohexene | NOCl + 4-methylcyclohexanol | 1-methoxy-5-phenyl-1-(4'-methylcyclohexyloxy)2-oximinocyclohexane |
| 22 | 3-methoxy cholestene-2 | methyl nitrite | 3,3-dimethoxy-2-oximinocholestane |

EXAMPLE 23

Production of 6-oximino-1,4-dioxaspiro[4,5]decane

A three-neck 500 ml. flask equipped with a serum capped inlet, a mechanical stirrer, inlets for the introduction of sulfur dioxide and hydrogen chloride, and a dry ice condenser protected with a nitrogen bubbler, was placed in a dry ice/acetone bath at −30°. A sulfur dioxide cylinder was connected to one inlet and about 125 ml. of sulfur dioxide was distilled into the flask. The stirrer was started and ethylene glycol (100 mmole, 5.60 ml.) was added by a syringe. Dry hydrogen chloride (125 mmole) was slowly bubbled into the solution and then cyclohexanone (100 mmole, 10.4 ml.) was added by a syringe. The hydrogen chloride inlet was removed and replaced with an inlet connected through a stopcock to a precooled flask containing 125 mmole (8.16 g.) of liquid nitrosyl chloride. The dry ice/acetone bath was removed and the reaction solution allowed to come to reflux (2°-10°). The stopcock on the nitrosyl chloride flask was then opened and the flask was gently warmed to allow the slow introduction of nitrosyl chloride vapors above the surface of the reaction solution. The addition was continued until the solution became pale orange (45 min.). The solution was stirred for another 15 min. and then poured into a 500 ml. predried and precooled flask. The reaction vessel was washed once with chloroform which was added to the sulfur dioxide solution. The flask was connected to a rotary evaporator and the solution was evaporated in vacuo at −20°. The last traces of sulfur dioxide were removed by the further addition of about 75 ml. of cold chloroform and re-evaporation. The resulting pale yellow oil was washed with the aid of chloroform into a 250 ml. beaker containing a stirring bar. The solution was diluted with chloroform to 150 ml., the stirrer was started, and the solution was neutralized to about pH 8 with either a paste of sodium bicarbonate or ammonia gas. The solution was dried by adding anhydrous magnesium sulfate and stirring for an additional few minutes. The salts were removed by filtration and the chloroform solution was concentrated to give 16.3–18.3 g. of a brown, viscous oil. Analysis of this oil by nmr indicated it to be about 80–90% 6-oximino-1,4-dioxaspiro[4,5]decane and about 10–20% 2-hydroxyethyl-6-oximinohexanoate. The product was isolated by either crystallization, distillation or column chromatography, m.p. 97°–98°.

EXAMPLES 24–29

The procedure of Example 23 has also been used to produce the following novel cyclic ketals from a cyclohexanone.

| Example | Cyclohexanone | Diol | Product | m.p. (° C.) | Yield (%) |
|---|---|---|---|---|---|
| 24 | cyclohexanone | 1,2-propanediol | 2-methyl-6-oximino 1,4-dioxaspiro-[4,5]decane | 115–117 | 70 |
| 25 | cyclohexanone | 3,-methyl-1,2-butanediol | 2-isopropyl-6-oximino-1,4-dioxaspiro[4,4]-decane | 62 | 60 |
| 26 | cyclohexanone | 1-phenyl-1,2-ethanediol | 2-phenyl-6-oximino-1,4-dioxaspiro[4,5]decane | 130–132 | 60 |
| 27 | cyclohexanone | cis-1,2-cyclohexanediol | 2'-oximinohexahydro spiro[1,3-benzodioxole-2,1'-cyclohexane] | 157–159 | 25 |
| 28 | 4-t-butyl-cyclohexanone | 1,2-ethanediol | 8-t-butyl-6-oximino-1,4-dioxaspiro[4,5] | 153–154 | 65 |
| 29 | 4-t-butyl-cyclohexanone | 1,2-propane diol | 8-t-butyl-2-methyl-6-oximino-1,4-dioxaspiro-[4,5]-decane | 119–125 | 50 |

EXAMPLES 30–31

The procedure of Example 23 can also be employed to produce the following novel cyclic ketals from a cyclohexanone.

| Example | Cyclohexanone | Diol | Product |
|---|---|---|---|
| 30 | 4-methyl cyclohexanone | 2,3-butanediol | 6-oximino-2,3,8-trimethyl-1,4-dioxaspiro[4,5] decane |
| 31 | 3-phenyl-cyclohexanone | 2,2-dimethyl-cis-3,4-butanediol | 3-t-butyl-6-oximino-9-phenyl-1,4-dioxaspiro[4,5]-decane |

EXAMPLE 32

Production of 6-oximino-1,4-dioxaspiro[4,5]decane

The same procedure as in Example 23 was used except 1,4-dioxaspiro[4,5]decane (14.2 g., 100 mmole) was used in place of the cyclohexanone and ethylene glycol.

EXAMPLES 33–34

The same method employed as in Example 32 can be used to produce the following novel compounds.

| Example | Cyclohexanone | Diiol | Product |
|---|---|---|---|
| 33 | cyclohexanone | 1,2-diphenyl-1,2-ethanediol | 2,3-diphenyl-6-oximino-1,4-dioxaspiro[4,5]decane |
| 34 | 4-t-butyl-cyclohexanone | 1,2-propanediol | 2-methyl-8-t-butyl-6-oximino-1,4-dioxa- |

| Example | Cyclohexanone | Diiol | Product |
|---|---|---|---|
| | | | spiro[4,5]decane |

We claim:
1. A process for the production of an α-nitrosoketal dimer of the formula

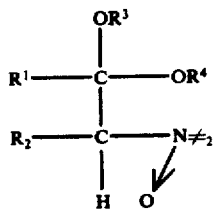

wherein $R^1$ and $R^2$ are selected from the group consisting of $C_1$–$C_{10}$ alkyl or phenyl and/or combinations thereof, or in combination together $R^1$ and $R^2$ are a part of the $C_5$–$C_{12}$ cyclic structures, and $R^3$ and $R^4$ are independently selected from the group consisting of $C_1$–$C_{10}$ alkyl, cyclohexyl and $C_1$–$C_4$ alkyl substituted cyclohexyl radicals, comprising the steps of:

a. nitrosating, in the presence of a catalytic amount of a suitable acid and at a temperature of between about −70° and 25° C and at a pressure of between about one atmosphere and 200 psi, an alkoxyalkene of the formula

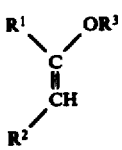

wherein $R^1$ and $R^2$ are selected from the group consisting of $C_1$–$C_{10}$ alkyl, phenyl and wherein both $R^1$ and $R^2$ are part of a $C_5$–$C_{12}$ carbo-cyclic structure, and $R^3$ is selected from the group consisting of $C_1$–$C_{10}$ alkyl, cyclohexyl and $C_1$–$C_4$ alkyl substituted cyclohexyl; with at least one molar equivalent of an alkyl nitrite of the formula $$R^4ONO$$

wherein $R^4$ is selected from the group consisting of $C_1$–$C_{10}$ alkyl, cyclohexyl and $C_1$–$C_4$ alkyl substituted cyclohexyl; and b. isolating the dimer thus formed.

2. The process of claim 1 wherein the alkyl nitrite is present in amount of 2–10 moles per mole of alkoxyalkene.

3. The process of claim 1 wherein the acid catalyst is sulfuric acid, sulfur trioxide, boron trifluoride etherate, ethyldimethoxycarbonium fluoroborate.

4. The process of claim 1 wherein the reaction is carried out in liquid sulfur dioxide using an alkyl nitrite in an amount of 1.10–1.50 moles per mole.

5. The process for the production of 1,1-dimethoxy-2-nitrosocyclohexane dimers comprising the steps of (a) nitrosating 1-methoxycyclohexene with 2–10 molar equivalents of methyl nitrite in the presence of 1.10–2.0 mole % of ethyldimethoxycarbonium fluoroborate catalyst at temperature between −30° and 25° C., and pressure of one atmosphere to 200 psi and;

b. evaporation of the excess of methyl nitrite, followed by addition of petroleum ether or other inert solvent, and filtration of the product.

* * * * *